US00PP20809P2

(12) United States Plant Patent
van Marrewijk

(10) Patent No.: US PP20,809 P2
(45) Date of Patent: Mar. 2, 2010

(54) ***GERANIUM* PLANT NAMED 'ABPP'**

(50) Latin Name: *Geranium×cantabrigiense*
Varietal Denomination: ABPP

(76) Inventor: Wim van Marrewijk, Lean van Vijververg 15, De Lier (NL) 2678

( * ) Notice: Subject to any disclaimer, the term of this patent is extended or adjusted under 35 U.S.C. 154(b) by 0 days.

(21) Appl. No.: 12/321,613

(22) Filed: Jan. 23, 2009

Related U.S. Application Data

(60) Provisional application No. 61/065,265, filed on Feb. 11, 2008.

(51) Int. Cl.
*A01H 5/00* (2006.01)

(52) U.S. Cl. ..... Plt./324

(58) Field of Classification Search ..... Plt./324
See application file for complete search history.

*Primary Examiner*—Sysan B McCormick Ewoldt

(57) ABSTRACT

A new cultivar of *Geranium* plant named 'ABPP' that is characterized by dense habit, dark-green divided foliage, and small deep-pink flowers on short stems held close to the foliage. In combination these traits set 'ABBP' apart from all other varieties of *Geranium* known to the inventor.

2 Drawing Sheets

Genus: *GERANIUM.*
Species: *×cantabrigiense.*
Denomination: 'ABPP'.

BACKGROUND OF THE INVENTION

This application claims the benefit of priority under 35 U.S.C. 119(e) of U.S. Provisional application Ser. No. 61/065,265 filed on Feb. 11, 2008, entitled *Geranium* Plant Named 'ABPP'.

The present invention relates to a new and distinct cultivar of cranesbill plant grown as an ornamental for use in border, rock garden, container, or groundcover for the landscape. The new cultivar, from the family Geraniaceae, is known botanically as *GERANIUM×cantabrigiense* and will be referred to hereinafter by the cultivar name 'ABPP'.

*Geranium* 'ABPP' was discovered by the inventor in 2003, as a naturally occurring whole plant mutation of an individual plant of *Geranium×cantabrigiense* 'Westray' (U.S. Plant Pat. No. 13,716). 'ABPP' was discovered growing within a commercial crop of *Geranium* 'Westray' at the inventor's nursery in Naaldwijk, The Netherlands.

'ABPP' is characterized by dense habit, dark green divided leaves, and flowers that are borne on short stems and are arranged closer to the foliage canopy than is typical of the parent or species. The small, profuse flowers are intense deep pink in color. 'ABPP' blooms in spring, from March to late June and sporadically through summer. Cultural requirements include full sun, well-draining soil, and moderate water. 'ABPP' is hardy in USDA Zone 6.

The closest comparison plant known to the inventor is the parent variety, *Geranium* 'Westray'. The new *Geranium* variety named 'ABPP' is mostly distinguishable from the parent by leaf size and by leaf and flower stem length. The leaves of 'ABPP' are approximately half the length and width of the leaves of 'Westray'. The petioles of 'ABPP' are approximately 4 cm in length, whereas the petioles of 'Westray' can extend to 10 cm in length. The peduncles of 'ABPP' are approximately 3 cm in length, whereas the peduncles of 'Westray' can extend to 20 cm in length. In combination, these characteristics of smaller leaf size and leaf and flower stem lengths confer a significantly more compact plant habit of 'ABPP' compared with 'Westray'.

In 2003 the inventor conducted the first asexual propagation of 'ABPP' at the inventor's nursery in The Netherlands, using the method of stem cuttings. Since that time, under careful observation, the distinguishing characteristics of 'ABPP' have been determined stable, uniform, and reproduce true to type in successive generations of asexual reproduction.

SUMMARY OF THE INVENTION

The following traits have been repeatedly observed and represent the distinguishing characteristics of the new *GERANIUM* plant named 'ABPP'. These traits in combination distinguish 'ABPP' from all other existing varieties of *Geranium* known to the inventor.

1. 'ABPP' exhibits dense habit.
2. The flowers of 'ABPP' are borne on short stems and are arranged closer to the foliage canopy, than is typical of the parent or species.
3. The flowers of 'ABPP' are intense-deep-pink in color.
4. The leaves of 'ABPP' are smaller and more profuse than observed on the parent variety or the species.
5. 'ABPP' flowers from March to late June continuing sporadically into August.
6. 'ABPP' is asexually propagated by the methods of stem cuttings, root cuttings, tip-cuttings, and division.
7. 'ABPP' is hardy to USDA Zone 6.

BRIEF DESCRIPTION OF THE DRAWINGS

The accompanying color drawings illustrate the overall appearance of the new variety named 'ABPP' showing color as true as is reasonably possible to obtain in color reproductions of this type.

The drawing labeled

The drawing labeled

Figure 1:
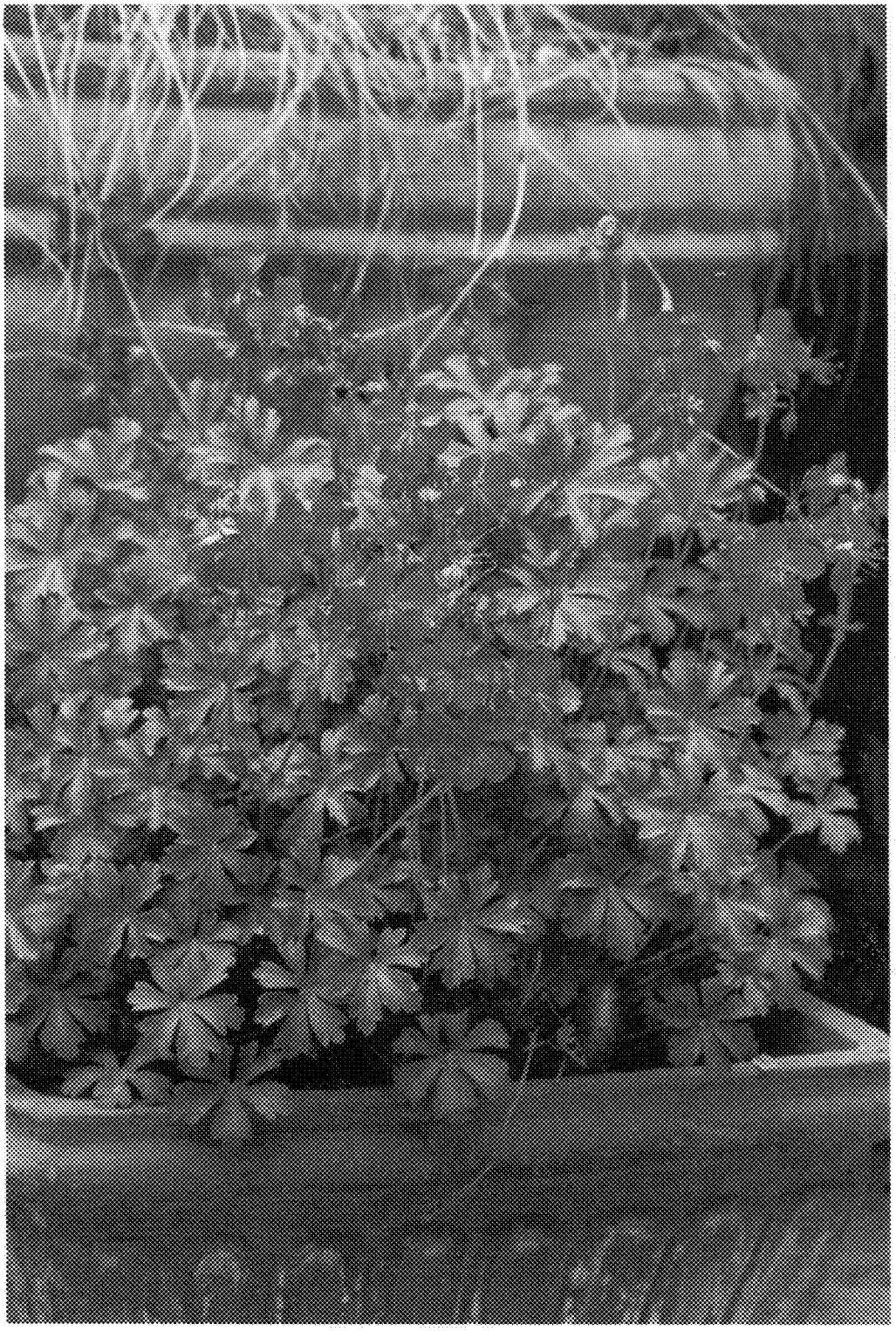
FIG. 1 depicts a 9-month-old plant in bloom growing out-of-doors in Arroyo Grande, Calif.
Figure 2:
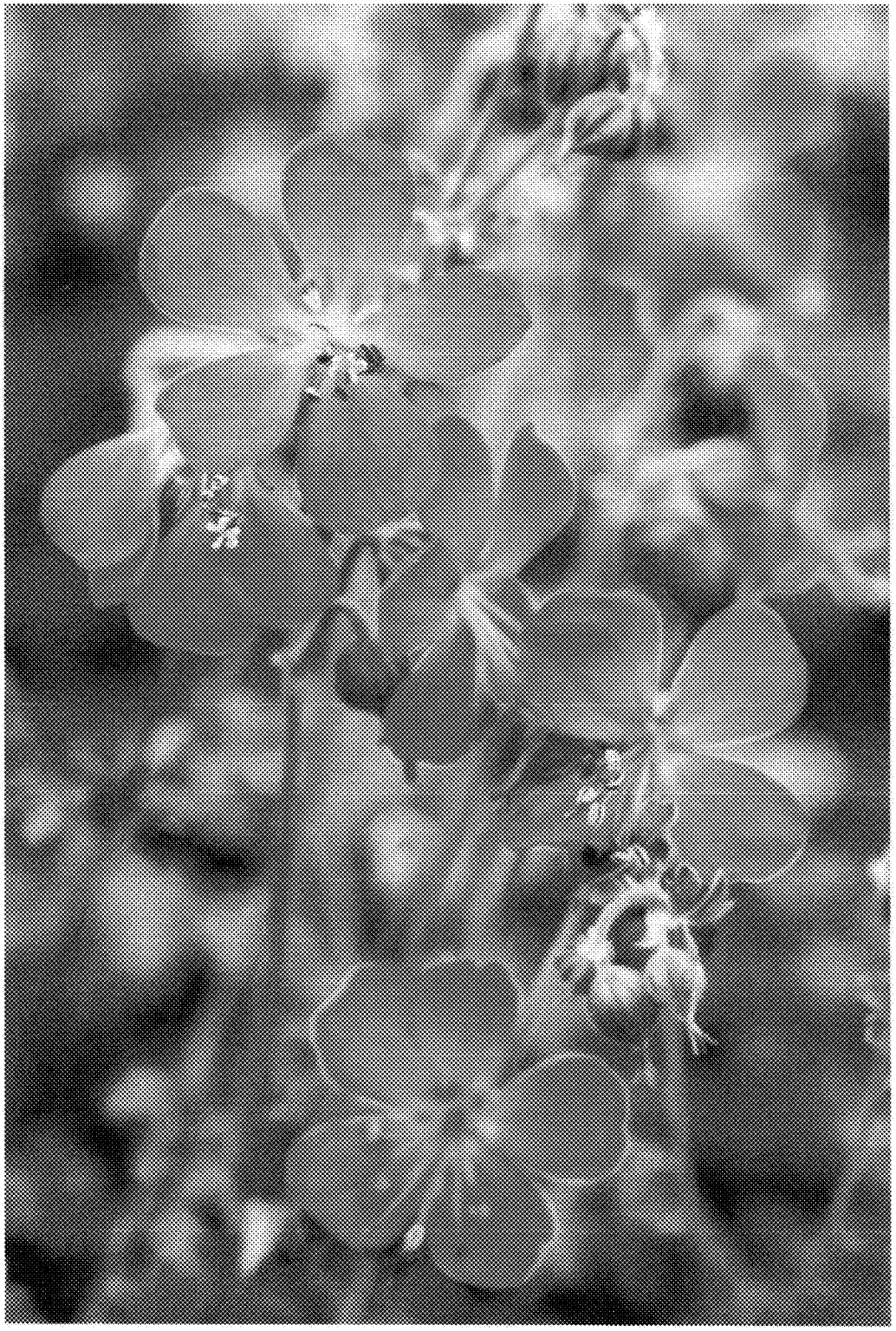
FIG. 2 depicts a close-up view of flowers and buds.

Color in the drawings may differ from color values cited in the detailed botanical description, which accurately describe the actual color of the new *Geranium* variety named 'ABPP'. Drawings were made using conventional techniques and although color may appear different from actual color due to light reflectance, they are as accurate as possible by conventional photography.

DETAILED BOTANICAL DESCRIPTION

The following is a detailed description of the new *Geranium* cultivar named 'ABPP'. Data was collected in Arroyo Grande Calif. from plants grown in 4 inch pots out-of-doors in a shade house. Color determinations are in accordance with the 2001 Royal Horticultural Society Colour chart except where general color terms of ordinary dictionary significance are used. The growing requirements are similar to the species.

Botanical classification: *GERANIUM×cantabrigiense* 'ABPP'.
Family: Geraniaceae.
Genus: *GERANIUM*.
Species: *×cantabrigiense*.
Denomination: 'ABPP'.
Common name: Cranesbill.
Parentage: *GERANIUM×cantabrigiense* 'ABPP' is a naturally occurring whole plant mutation derived from the following parent:
  *Parent plant.*—An individual *Geranium* 'Westray' (U.S. Plant Pat. No. 13,716).
Type: Ornamental.
Use: Border, rock garden, container, or groundcover for the landscape.
Commercial classification: Flowering perennial.
Vigor: Vigorous.
Root system: Fine.
Habit: Dense.
Height (in liner pot): 6 cm.
Width (with flower stalks): 28 cm.
Hardiness: USDA Zone 6.
Seasonal interest: Flowers bloom in spring from March through June and sporadically through summer.
Propagation methods: Stem cuttings, root cuttings, tip-cuttings, and division.
Cultural conditions: Full sun to filtered light, well-draining soil, and moderate water.
Crop time (range): 4–5 months are needed to produce a finished 1-liter container from a rooted cutting or division.
Rooting time (average): 3 weeks are needed for an initial cutting to produce roots.
Susceptibility to pests and disease: No known susceptibility to pests or diseases observed to date.
Stem:
  *Stem shape.*—Sub-cylindrical.
  *Stem color.*—144A.
  *Stem surface.*—Pubescent.
  *Stem dimensions.*—4 cm. in length and 1 mm. in diameter.
  *Internode length* (*average*).—5 cm.
Foliage:
  *Leaf arrangement.*—Basal rosette.
  *Leaf quantity* (*average*).—30 per liner pot.
  *Leaf division.*—Palmately divided.
  *Lobes.*—5 in number.
  *Leaf margins.*—Toothed.
  *Leaf shape.*—Reniform.
  *Leaf base.*—Auriculate.
  *Leaf Apex.*—Acute.
  *Leaf venation.*—Pinnipalmate.
  *Vein color* (*abaxial surface*).—146C.
  *Vein color* (*adaxial surface*).—146C.
  *Leaf surface* (*abaxial*).—Glabrous.
  *Leaf surface* (*adaxial*).—Puberulent.
  *Leaf length* (*range*).—1.50–3.25 cm. in length.
  *Leaf width* (*range*).—1.50–3.25 cm. in width.
  *Leaf color* (*abaxial surface*).—146C.
  *Leaf color* (*adaxial surface*).—136B.
  *Attachment.*—Petiolate.
  *Petiole surface.*—Puberulent.
  *Dimensions of petiole.*—4 cm. in length and 1 mm. in diameter.
  *Petiole shape.*—Cylindrical.
  *Color of petiole.*—144A.
  *Stipules.*—None observed.
  *Foliar fragrance.*—Resinous lemon scent.
Flower:
  *Inflorescence.*—Cyme.
  *Flower arrangement.*—Double.
  *Flower quantity* (*range*).—15–20 per liner pot.
  *Flower shape.*—Rotate.
  *Flower depth* (*range*).—1.40–2 cm.
  *Flower diameter* (*average*).—2.10 cm.
  *Aspect.*—Facing upward and outward.
  *Self-cleaning or persistent.*—Persistent.
  *Flower color.*—Ranges between N66C and 71C.
  *Petals.*—5 in number.
  *Petal dimensions.*—1.0 cm. in length and 0.90 cm. in width.
  *Petals fused or unfused.*—Unfused.
  *Petal margin.*—Entire.
  *Petal apex* (*range*).—Emarginate to obtuse.
  *Petal base.*—Attenuate.
  *Petal shape.*—Obovate.
  *Petal surface* (*abaxial and adaxial*).—Glabrous.
  *Petal appearance.*—Irridescent.
  *Petal color* (*abaxial surface*).—71C.
  *Petal color* (*adaxial surface*).—Ranges between N66C and 71C.
  *Bud color.*—75B.
  *Bud shape.*—Ovoid.
  *Bud apex.*—Rounded.
  *Bud surface.*—Pubescent.
  *Bud dimensions.*—7 mm. in length and 5 m. in width.
  *Sepals.*—5 in number.
  *Sepals fused or unfused.*—Unfused.
  *Sepal margin.*—Entire.
  *Sepal apex.*—Caudate.
  *Calyx dimensions.*—1 cm. in height and 0.70 cm. in diameter.
  *Calyx surface:* (*abaxial and adaxial*).—Villous and ribbed.
  *Calyx shape.*—Urceolate.
  *Calyx color.*—71A and 146A both present.
  *Pedicel shape.*—Cylindrical.
  *Pedicel surface.*—Pubescent.
  *Pedicel color.*—183C.
  *Pedicel dimensions.*—1 cm. in length and 2 mm. in diameter.
  *Peduncle shape.*—Cylindrical.
  *Peduncle surface.*—Glabrous.
  *Peduncle color.*—146A.
  *Peduncle dimensions.*—3 cm. in length and 1.50 mm. in diameter.

*Subtending leaf.*—Quantity (average): 6 per peduncle. Arrangement: Opposite. Dimensions: 1 cm. in length and 1 mm. in width. Color (abaxial and adaxial surfaces): 136A. Division: Palmate. Apex: Acute. Base: Auriculate. Margin: Entire. Surface (abaxial and adaxial): Glabrous. Color (abaxial surface): N138B. Color (adaxial surface): 139A.

*Flower fragrance.*—Slight resinous lemon scent.

Reproductive organs:

*Stamens.*—6 in number.

*Stamen color.*—75C.

*Stamen length* (*average*).—6 mm.

*Anther.*—6 in number.

*Anther length* (*average*).—3 mm.

*Anther color.*—183A.

*Pollen.*—None observed to date.

*Pistil.*—4 in number.

*Pistil shape.*—Filamentous.

*Pistil color.*—71B.

*Pistil length* (*range*).—1–2 cm.

*Stigma.*—1 in number

*Stigma shape.*—5-lobed.

*Stigma color.*—71B.

*Stigma dimensions.*—3 mm. in diameter and 3 mm. in height.

*Ovary position.*—Superior.

*Ovary shape.*—Elongated oval.

*Ovary dimensions.*—6 mm. in height and 2.50 mm. in diameter.

*Ovary color.*—144C.

Seed: None observed to date.

The invention claimed is:

1. A new and distinct variety of *Geranium* plant named 'ABPP' as described and illustrated herein.

* * * * *